US005410605A

United States Patent [19]

Sawada et al.

[11] Patent Number: 5,410,605

[45] Date of Patent: Apr. 25, 1995

[54] ACTIVE VIBRATION CONTROL SYSTEM

[75] Inventors: Hideshi Sawada; Hisashi Sano, both of Wako, Japan

[73] Assignee: Honda Giken Kogyo Kabushiki Kaisha, Tokyo, Japan

[21] Appl. No.: 902,247

[22] Filed: Jun. 22, 1992

[30] Foreign Application Priority Data

Jul. 5, 1991 [JP] Japan ................................ 3-190970

[51] Int. Cl.$^{6}$ ................................ A61F 11/06

[52] U.S. Cl. ................................ 381/71

[58] Field of Search ................................ 381/71, 94

[56] References Cited

U.S. PATENT DOCUMENTS 4,423,289 12/1983 Swinbanks ................................ 381/71

5,131,047 7/1992 Hashimoto et al. ................................ 381/71

5,170,433 12/1992 Elliott et al. ................................ 381/71

FOREIGN PATENT DOCUMENTS 1-501344 5/1989 Japan .

2054999 2/1981 United Kingdom .

2107960 5/1983 United Kingdom .

*Primary Examiner*—Curtis Kuntz

*Assistant Examiner*—Ping W. Lee

*Attorney, Agent, or Firm*—Nikaido, Marmelstein, Murray & Oram

[57] ABSTRACT

An adaptive control circuit is responsive to a reference signal, i.e. an output from a sensor which senses vibration from a vibration source, for generating a cancelling signal having a transfer characteristic inverse to a transfer characteristic of vibration from the vibration source to a human body. A loud speaker is responsive to an output from the adaptive control circuit for generating cancelling vibration. A microphone senses an error between the vibration from the vibration source and the cancelling vibration from the loud speaker and generates an error signal indicative of the sensed error. The adaptive control circuit varies the inverse transfer characteristic by an amount corresponding to the error signal so as to minimize the above error. A divided processing circuit divides the output from the sensor into vibration components falling respectively within a plurality of frequency ranges and separately processes the divided vibration components. The divided processing circuit has a sampling circuit which samples the divided vibration components at different sampling periods between the above frequency ranges.

5 Claims, 7 Drawing Sheets

ACTIVE VIBRATION CONTROL SYSTEM

BACKGROUND OF THE INVENTION

1. Field of the Invention

This invention relates to an active vibration control system, and more particularly to an active vibration control system for suppressing vibrations or noise generated from prime movers or load devices driven thereby such as compressors and generators, or from apparatus equipped with engine exhaust mufflers or like intake and/or exhaust systems, or from running vehicles.

2. Prior Art

The term "vibration" used throughout the present specification includes not only vibration in its proper or literal meaning but also noise and sound.

Conventional active vibration control systems of this kind include a system which has been proposed by Japanese Provisional Patent Publication (Kohyo) No. 1-501344. The proposed system comprises, as shown in FIG. 1, a noise (vibration) source, an adaptive control circuit 102 which receives an output from the vibration sensor 101 as a reference signal and generates, based upon the reference signal, a cancelling signal having a transfer characteristic inverse to a transfer characteristic of vibration from the vibration source to a human body, a loud speaker 103 as cancelling vibration-generating means responsive to an output from the adaptive control circuit 102 for generating cancelling noise (cancelling vibration), and a microphone 104 as an error sensor for sensing a cancelling error between noise from the noise source and the cancelling noise from the loud speaker 103.

According to the above adaptive control circuit, noise (primary noise) picked up by the noise sensor 101 is sampled by an A/D converter 105, which supplies the resulting digital data as the reference signal X to the adaptive control circuit 102. The adaptive control circuit 102 in turn generates and supplies the cancelling signal to a D/A convertor 106 to be converted to a signal which drives the loud speaker 103 to generate cancelling noise (secondary noise).

On the other hand, the microphone 104 senses the cancelling error between the cancelling noise from the loud speaker 103 and the noise (primary noise) from the noise source, and the sensed cancelling error is sampled by an A/D convertor 107 into an error signal $\epsilon$ as digital data, which is fed back to the adaptive control circuit 102. Thus, the active vibration control system operates to vary the above-mentioned inverse transfer characteristic of the cancelling signal so as to minimize the value of the error signal indicative of the cancelling error between the primary noise and the secondary noise, to thereby suppress the noise from the noise source.

In the active vibration control system disclosed by Kohyo No. 1-501344, the adaptive control circuit 102 contains two FIR type adaptive digital filters (ADF) which selectively process only fundamental frequency components of the noise and higher harmonic components thereof.

The adaptive control circuit 102 also contains adaptive algorithm as a procedure for creating an optimal cancelling signal, which generally comprises LMS algorithm (Least Mean Square Method).

FIG. 2 shows another conventional active vibration control system which is a so-called multi-channel type active vibration control system capable of suppressing noise from a plurality of noise sources (vibration sources). This active vibration control system is comprised of noise sensors $\mathbf{108}_1$–$\mathbf{108}_n$, A/D converters $\mathbf{109}_1$–$\mathbf{109}_n$, D/A converters $\mathbf{110}_1$–$\mathbf{110}_n$, loud speakers $\mathbf{111}_1$–$\mathbf{111}_n$, microphones $\mathbf{112}_1$–$\mathbf{112}_n$, A/D converters $\mathbf{113}_1$–$\mathbf{113}_n$, n being equal to the number of the noise sources, and one adaptive control circuit 114 which operates to minimize the error between noise from the noise sources (primary noise) and cancelling noise (secondary noise).

The adaptive control circuit 114 contains a number n of control circuits provided respectively for the loud speakers $\mathbf{111}_1$–$\mathbf{111}_n$, which create cancelling signals for cancelling noise from the respective corresponding noise sources.

However, according to the above-mentioned conventional active vibration control systems, the frequency range of noise to be suppressed is limited to a low frequency range. In the system disclosed in Kohyo No. 1-501344 employing a plurality of adaptive digital filters for a single vibration source, only the fundamental frequency components and its higher harmonic components are selectively processed. That is, the conventional systems are not intended to suppress noise over its entire frequency range. Further, the adaptive digital filters used in these systems have such characteristics as to be able to suppress only low frequency noise components, making it impossible to process noise over a wide frequency range thereof.

For example, to suppress so-called random noise which has a wide frequency range, a system is required, which has the ability to suppress wide frequency range components. However, the conventional systems, which have low accuracy of cancelling noise components in a high frequency range, cannot satisfy such requirements, though they can suppress noise components in a low frequency range.

Moreover, component devices such as the noise sensors as vibration-sensing means, the error sensors, and the loud speakers as the cancelling vibration-generating means do not have uniform characteristics over the entire frequency range. However, in actuality, as each component device a single type is used, thus making it impossible to obtain satisfactory noise suppression effects over the entire frequency range.

SUMMARY OF THE INVENTION

It is, therefore, the object of the invention to provide an active vibration control system which is capable of providing satisfactory noise suppression effects over the entire frequency range.

To attain the above object, the present invention provides an active vibration control system includes:

at least one vibration source;

at least one first sensor device for sensing vibration from the vibration source;

control device disposed to receive an output from the first sensor device as a reference signal, the control device being responsive to the reference signal for generating a cancelling signal having a transfer characteristic inverse to a transfer characteristic of vibration from the vibration source to a human body;

cancelling vibration-generating device responsive to an output from the control device for generating cancelling vibration; and second sensor device for sensing an error between the vibration from the vibration source and the cancelling vibration from the cancelling vibration-generating device and generating an error signal indicative of the sensed error, wherein the control device varies the inverse transfer characteristic of the cancelling signal by an amount corresponding to a value of the error signal so as to minimize the error.

The control device includes divided processing device for dividing inputs from the first and second sensor devices into vibration components falling respectively within a plurality of frequency ranges and separately processing the divided vibration components, the divided processing device having sampling device for sampling the divided vibration components at different sampling periods between the frequency ranges.

The above plurality of frequency ranges include a high frequency range and a low frequency range. Preferably, the sampling device oversamples vibration components within the high frequency range at a shorter period and downsamples vibration components within the low frequency range at a longer period.

Also preferably, the divided processing device processes the vibration components by the use of different algorithmic method between the frequency ranges.

Further preferably, the divided processing device includes oversampling device for oversampling outputs from the first and second sensor devices, filter device for dividing the oversampled outputs from the first and second sensor devices into vibration components falling within the high frequency range and vibration components falling within the low frequency range, and downsampling device for downsampling the vibration components falling within the low frequency range.

In an embodiment of the invention, the active vibration control system includes single cancelling vibration-generating device forming the above cancelling vibration-generating device, and synthetic inputting device for synthesizing a plurality of cancelling signals formed by processing the vibration components within the frequency ranges by the divided processing device and inputting the synthesized cancelling signal to the single cancelling vibration-generating device.

In a further embodiment of the invention, the active vibration control system includes a plurality of cancelling vibration-generating devices forming the cancelling vibration-generating device and corresponding, respectively, to the frequency ranges, and separate inputting device for separately inputting a plurality of cancelling signals formed by processing the vibration components within the frequency ranges by the divided processing device, respectively, to the cancelling vibration-generating device.

In a still further embodiment of the invention, the active vibration control system includes a plurality of cancelling vibration-generating device forming the cancelling vibration-generating device and corresponding, respectively, to the frequency ranges, and separate inputting device for separately inputting a plurality of cancelling signals formed by processing the vibration components within the frequency ranges by the divided processing device, respectively, to the cancelling vibration-generating device, the second sensor device comprising a plurality of sensors corresponding, respectively, to the frequency ranges.

The above and other objects of the invention will be more apparent from the following detailed description taken in conjunction with the accompanying drawings.

BRIEF DESCRIPTION

DETAILED DESCRIPTION

Figure 1:
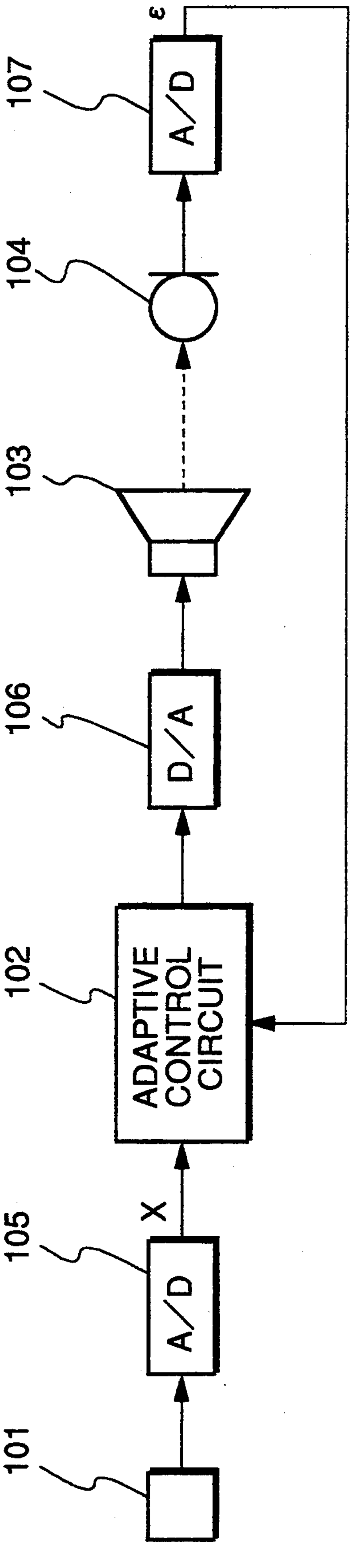
FIG.1 PRIOR ART
FIG. 1 is a block diagram showing the arrangement of a conventional active vibration control system.
Figure 2:
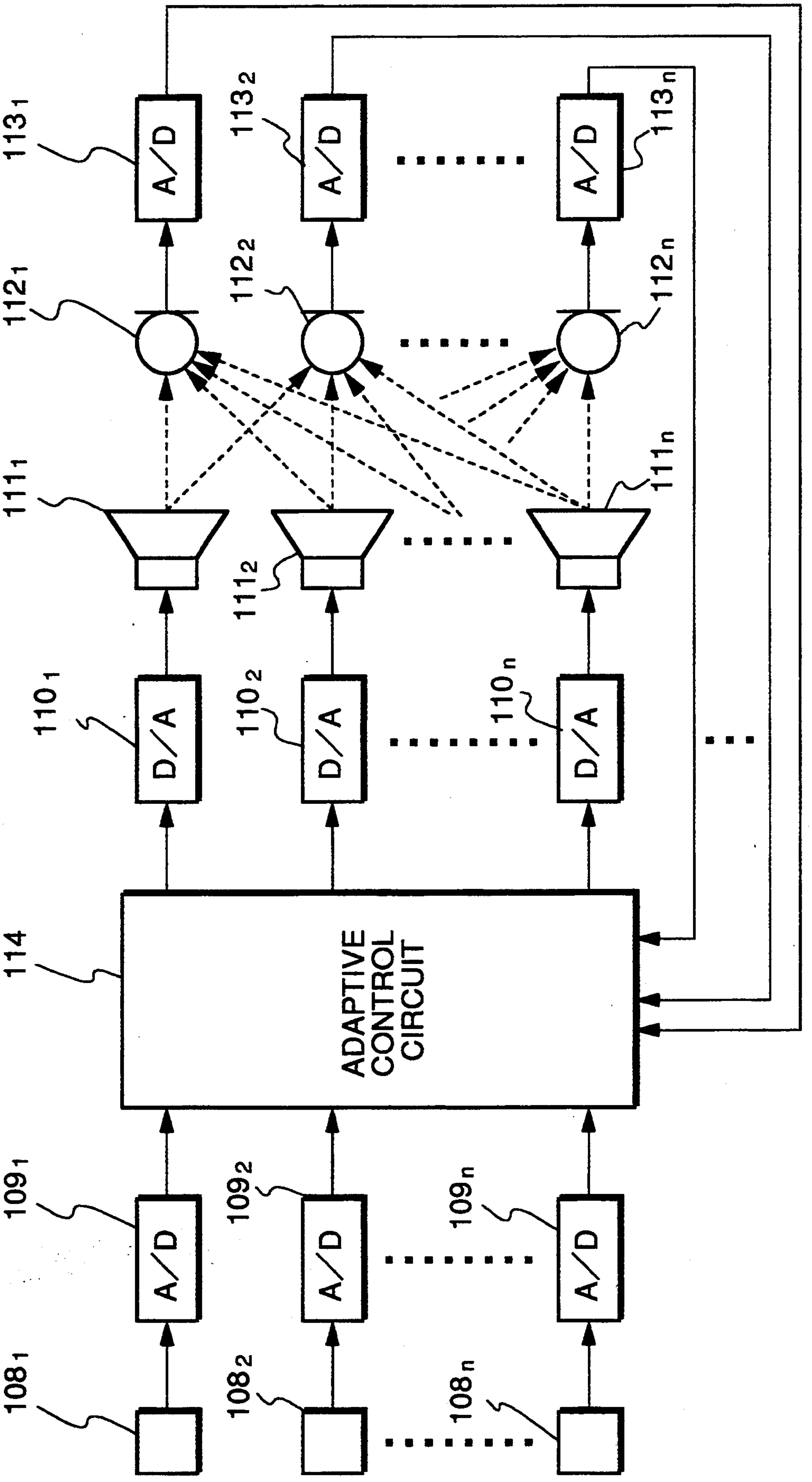
FIG.2 PRIOR ART
FIG. 2 is a block diagram showing the arrangement of another convention active vibration control system.

The invention will now be described in detail with reference to the drawings showing embodiments thereof. In FIGS. 3–6, corresponding elements are designated by identical corresponding reference numerals.

Figure 3:
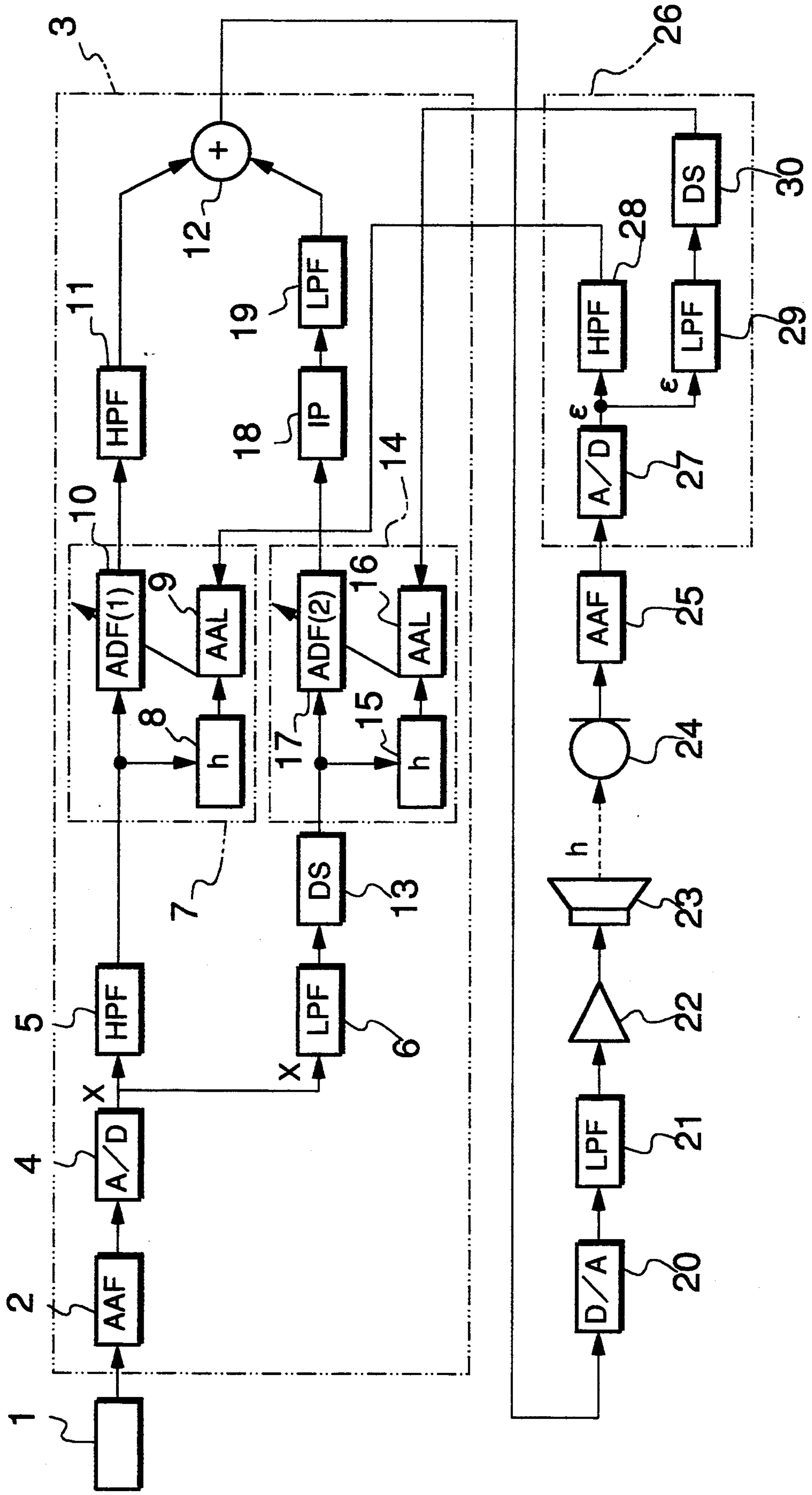
FIG. 3 is a block diagram showing the arrangement of an active vibration control system according to a first embodiment of the present invention.

Referring first to FIG. 3, there is shown an active vibration control system according to a first embodiment of the invention. In the figure, reference numeral 1 designates a noise sensor which senses noise such as noise from a running vehicle (noise source) and noise from an engine (noise source) installed in the vehicle. A signal indicative of noise sensed by the noise sensor 1 is supplied to an anti-aliasing filter (AAF) 2 which cuts off frequency components in the noise higher than a predetermined frequency, i.e. sets a particular frequency band which is to be controlled, the cut-off frequency thereof being set to a desired frequency depending upon the use of the system.

A noise signal from the anti-aliasing filter 2 is delivered to a first divided processing circuit 3 wherein the noise signal is divided into high frequency-band components and low frequency-band components to process the divided noise components in respective appropriate manners.

More specifically, the noise signal from the anti-aliasing filter 2 is subjected to oversampling (e.g. at a sampling frequency twice, 4 times, . . . n times as high as the usual sampling frequency) by the A/D converter 4, and the resulting digital data is supplied as a reference signal X to a high-pass filter (HPF) 5 and a low-pass filter (LPF) 6 whereby the reference signal X is divided into high frequency-band components and low frequency-band components.

Since the reference signal X is obtained by oversampling the noise signal by the A/D converter 4, as mentioned above, the anti-aliasing filter 2 can be designed to have a gentle cut-off characteristic, to enable minimizing the phase distortion and the delay time (transfer time lag). Particularly, it is desired that the anti-aliasing filter 2 should have a short delay time since if the delay time is long, the causality might not be satisfied. In this embodiment, by obtaining the reference signal X through oversampling, the cut-off characteristic of the anti-aliasing filter 2 can be designed gentle to thereby shorten the delay time.

The reference signal X components (high frequency-band components) passing through the high-pass filter 5 is delivered to a high frequency-band adaptive control circuit 7. The adaptive control circuit 7 is comprised of a filter 8 for compensating for a transfer characteristic between a loud speaker and a microphone, hereinafter referred to, an adaptive algorithm (AAL) processor 9 for calculating an inverse transfer characteristic which is inverse in phase to a transfer characteristic from the noise source to an occupant (the microphone), based upon the reference signal and an error signal from an error sensor, hereinafter referred to, and an FIR type adaptive digital filter (ADF (1)) 10 for generating a cancelling signal having the inverse transfer characteristic calculated by the processor 9. The adaptive digital filter 10 is of a type adapted for processing of a high frequency range.

The high frequency-band adaptive control circuit 7, which is supplied with the reference signal X obtained through oversampling and hence retaining even accurate information on short waveform components within the high frequency-band, can carry out signal processing with high accuracy to effectively suppress the noise.

Since the reference signal X obtained through oversampling is directly input to the high frequency-band adaptive control circuit 7, the adaptive digital filter 10 is required to have a very long tap length to match the high sampling speed. Accordingly, the adaptive algorithm should be of a simple-processing type having a high speed convergence to the optimal solution (approximate solution), such as the LMS method and the FK method.

The cancelling signal from the high frequency-band adaptive control circuit 7 is delivered via a high-pass filter (HPF) 11 to an adder 12.

On the other hand, the reference signal X components (low frequency-band components) passing through the low-pass filter 6 are subjected to downsampling by a downsampling circuit 13, and the downsampled components are supplied to a low frequency-band adaptive control circuit 14. That is, since the processing of low frequency-band components need not be high speed processing, the reference signal X components obtained through oversampling and passing through the low-pass filter 6 are "thinned out" to a required low sampling rate.

Similarly to the high frequency-band adaptive control circuit 7, the low frequency-band adaptive control circuit 14 is comprised of an FIR type filter 15 adapted for processing of the low frequency-band, an adaptive algorithm processor (AAL) 16, and an FIR type adaptive digital filter (ADF (2)) 17.

The low frequency-band adaptive control circuit 14, which is supplied with the downsampled reference signal X components, can be designed to have a low sampling rate and reduced numbers of delay elements of the filter 15 and taps of the adaptive digital filter 17. Further, the adaptive digital filter 17 can have a longer time for adaptive processing by virtue of the low sampling rate and the short tap length. Therefore, the adaptive algorithm can be of a type having high identification accuracy though such type generally requires somewhat complicated processing, such as a learning identification method, the RLS method, and the LMS method.

The cancelling signal from the low frequency-band adaptive control circuit 14 is supplied to an interpolation circuit (IP) 18 where the cancelling signal is subjected to interpolation to match the sampling period of the cancelling signal from the low frequency-band adaptive control circuit 14 with the sampling period of the cancelling signal from the high frequency-band adaptive control circuit 7.

The interpolated cancelling signal is delivered via a low-pass filter (LPF) 19 to the adder 12. Thus, the two cancelling signals are added together by the adder 12. An output from the adder 12, i.e. a synthetic cancelling signal is converted to an analog signal by a D/A converter 20. The analog-converted synthetic cancelling signal is delivered through a low-pass filter (LPF) 21 and an amplifier 22 to be outputted in the form of cancelling sound from a loud speaker 23.

The cancelling sound emitted from the loud speaker 23 is received by a microphone 24 after being given a certain transfer characteristic h, together with noise (primary noise) directly transmitted from the noise source. An output from the microphone, indicative of the difference between the cancelling sound and the primary noise is supplied to a second divided processing circuit 26 via an anti-aliasing filter (AAF) 25.

In the second divided processing circuit 26, the output from the microphone 24 via the anti-aliasing filter 25 is oversampled by an A/D converter 27 with the same period as the sampling period of oversampling by the A/D converter 4 of the first divided processing circuit 3 to be converted to an error signal $\epsilon$ as digital data. The error signal $\epsilon$ is supplied to both a high-pass filter (HPF) 28 and a low-pass filter (LPF) 29.

An error signal component passing through the high-pass filter 28 is fed back to the high frequency-band adaptive control circuit 7 which operates in response to the error signal $\epsilon$ to vary the inverse transfer characteristic of the cancelling signal to be output, so as to minimize the value of the error signal $\epsilon$.

On the other hand, an error signal component passing through the low-pass filter 29 is thinned out by a downsampling circuit to match its sampling period with that of the reference signal X input to the low frequency-band adaptive control circuit 14, and the thinned-out error signal $\epsilon$ is fed back to the low frequency-band adaptive control circuit 14 which varies the inverse transfer characteristic of the cancelling signal to be output, in response to the error signal $\epsilon$, in a manner similar to the processing of the high frequency-band adaptive control circuit 7.

In this way, according to the active vibration control system of the present embodiment, the frequency range of noise from the noise source is divided into a high frequency range and a low frequency range by the first and second divided processing circuits 3, 26, and the two frequency range components are processed by the respective adaptive control circuits 7, 14 in manners appropriate to the respective frequency ranges, to thereby enable suppressing the noise to a desired extent over the entire frequency range.

Figure 4:
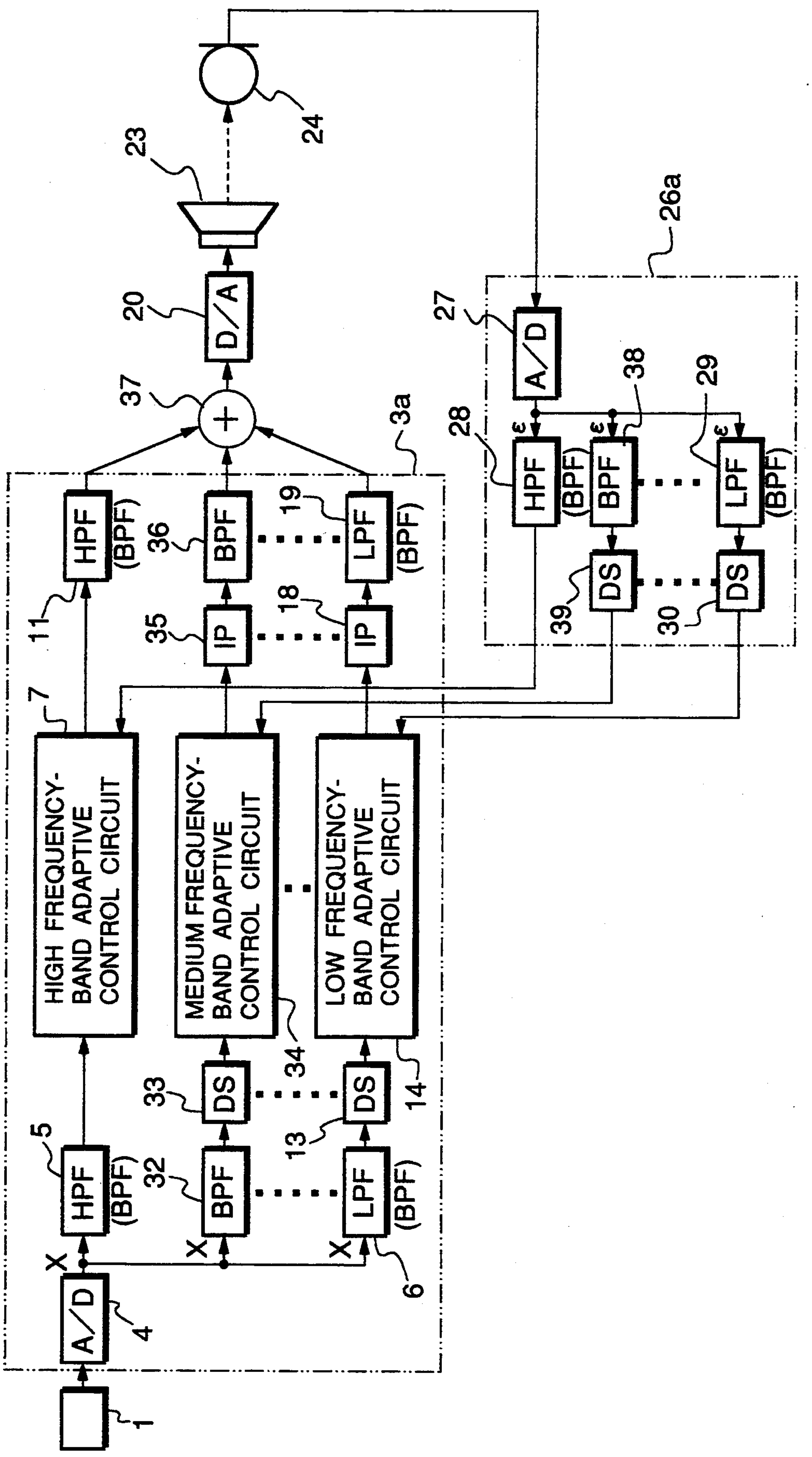
FIG. 4 is a block diagram showing the arrangement of a second embodiment of the invention.

FIG. 4 shows an active vibration control system according to a second embodiment of the invention. This embodiment is distinguished from the first embodiment described above in that noise from a noise source is divided into three or more frequency bands by three or more divided processing circuits (first and second divided processing circuits 3*a*, 26*a*).

More specifically, in the second embodiment, the first and second divided processing circuits 3*a*, 26*a* each include a plurality of band pass filters (BPF) 32, 38 each having a cut-off characteristic for passing a medium range between a high frequency range and a low frequency range. In a manner similar to the above described first embodiment, noise from a noise source is supplied to and processed by the band pass filters 32, downsampling circuits 33, medium frequency-band adaptive control circuits 34, interpolation circuits 35, and band pass filters (BPF) 36, and the resulting cancelling signals are supplied to an adder 37 where they are added together with cancelling signals from a high pass filter (HPF) 11 and a low pass filter (LPF) 19. The resulting synthetic cancelling signal is converted to an analog signal by a D/A converter 20 to be output from a loud speaker 23.

The resulting error signal $\epsilon$ from a microphone 24 is processed similarly to the manner described above. In this embodiment, components in the error signal $\epsilon$ falling within the medium frequency range from the band pass filters 38 are delivered through downsampling circuits 39 to be fed back to the medium frequency-band adaptive control circuits 34.

Thus, according to this embodiment, the medium frequency range between the high frequency range and the low frequency range is divided into a plurality of frequency bands, and the components within the medium frequency bands are processed by the respective medium frequency-band adaptive control circuits 34 to form cancelling signals, based upon which adaptive control is carried out to minimize the error signal $\epsilon$, to thereby further effectively suppress the noise.

Figure 5:
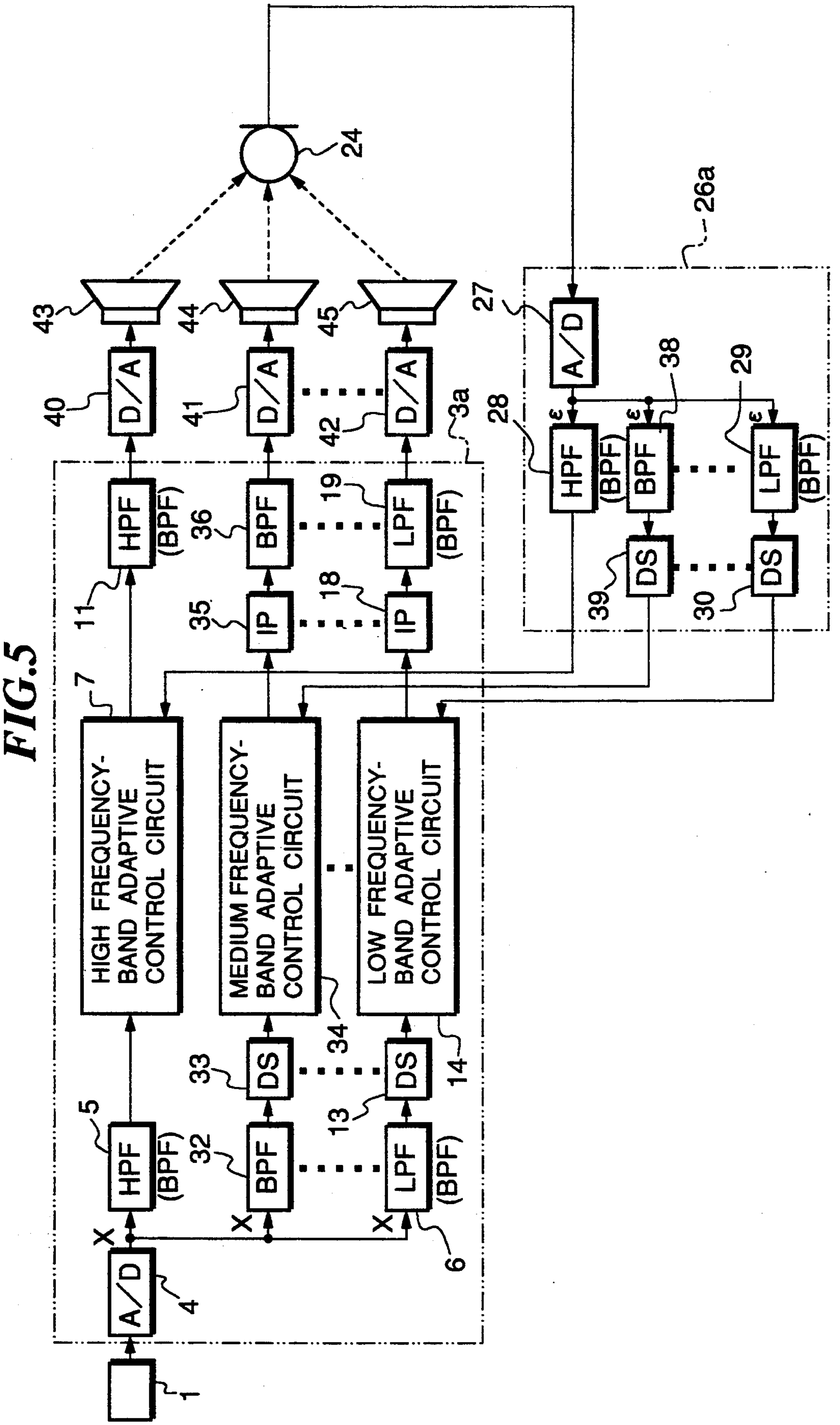
FIG. 5 is a block diagram showing the arrangement of a third embodiment of the invention.

FIG. 5 shows a third embodiment of the invention. This embodiment is distinguished from the second embodiment described above in that instead of providing the adder 37 in FIG. 3, a plurality of D/A converters 40, 41 . . . , 42 and as many loud speakers 43, 44 . . . , 45 are provided.

According to the third embodiment, advantageouly the loud speakers 43, 44 . . . , 45 can have different characteristics from each other, i.e. suitable for the respective frequency-bands, and hence have enhanced responsiveness, to thereby obtain more accurate cancelling effects over the entire frequency range and therefore enable to further effectively suppress the noise.

Figure 6:
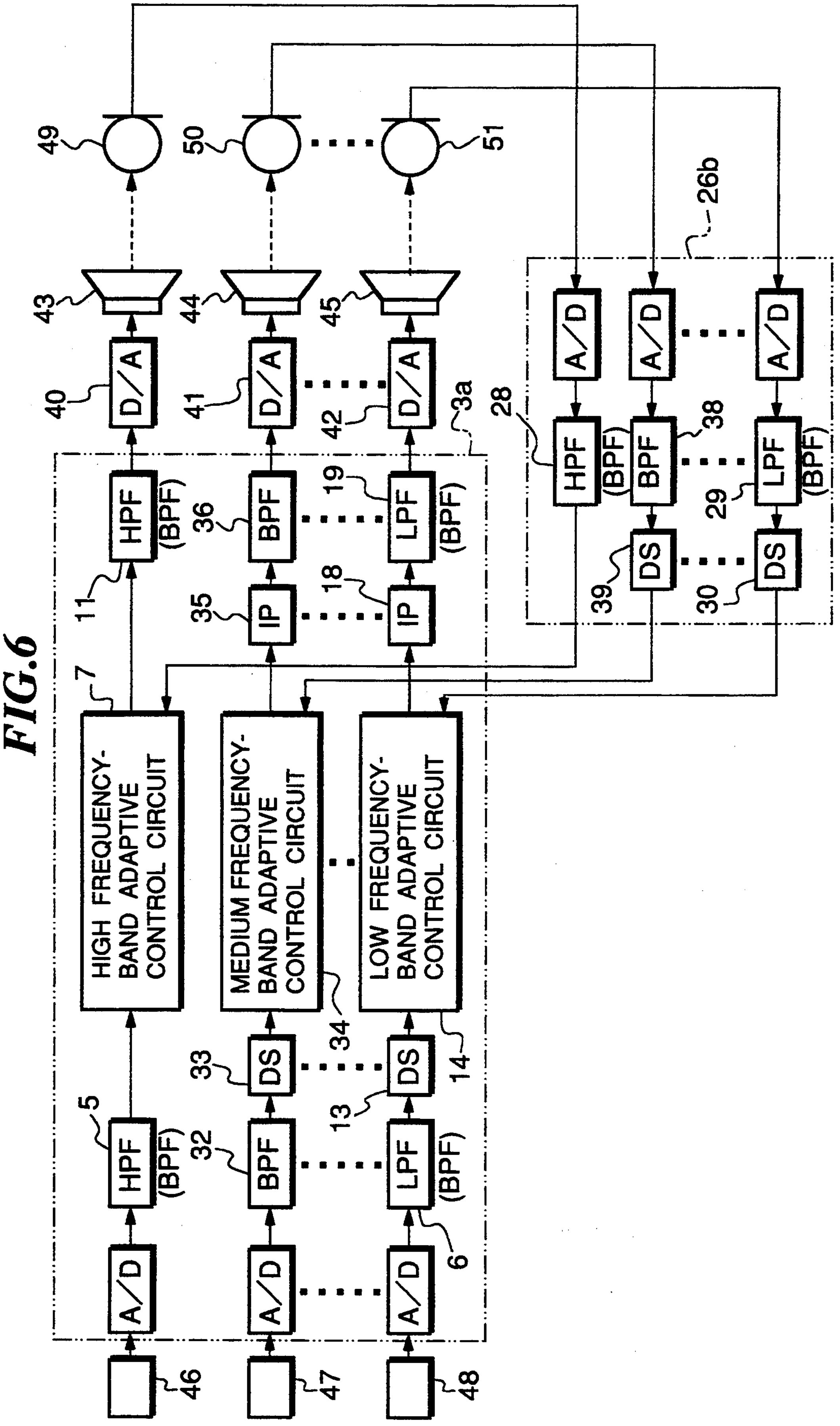
FIG. 6 is a block diagram showing the arrangement of a fourth embodiment of the invention.

FIG. 6 shows a fourth embodiment of the invention. This embodiment is distinguished from the third embodiment described above in that a plurality of noise sensors 46, 47 . . . , 48 and as many microphones 49, 50 . . . , 51 are provided for as many divided frequency ranges.

According to the fourth embodiment, advantageously the noise sensors and the microphones can have different characteristics suitable for the respective frequency-bands, to enhance the accuracy of sensing the reference signal X and the error signal $\epsilon$.

Figure 7:
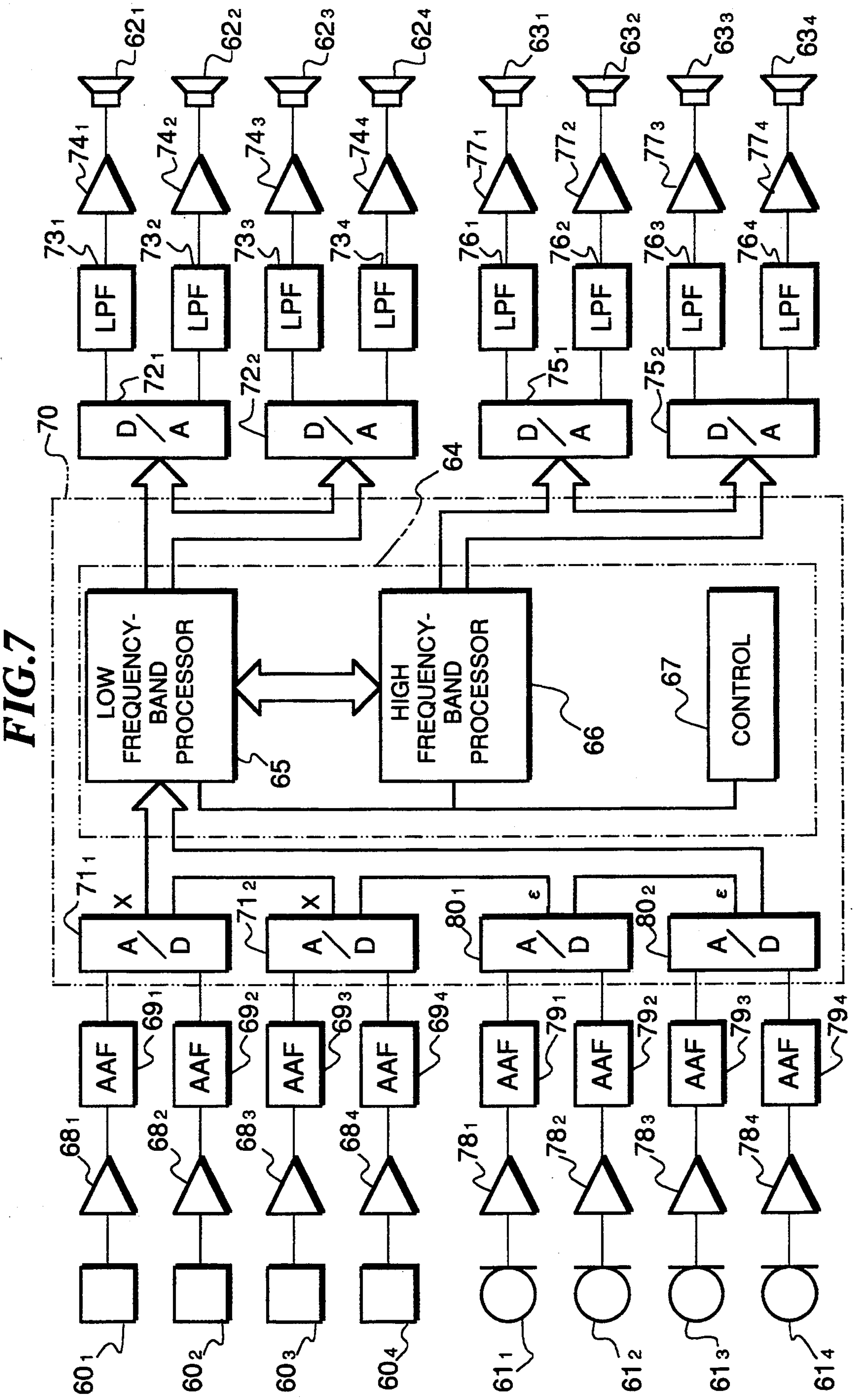
FIG. 7 is a block diagram showing the arrangement of a fifth embodiment of the invention.

FIG. 7 shows, by way of an example, a road noise control system (a system for supressing road noise generated during running of a vehicle due to uneveness of the road surface) to which is applied the active vibration control system according to the invention. In this example, four noise sensors $60_1$–$60_4$ formed of acceleration pickups or the like are provided for each wheel, not shown, of the vehicle as a noise source (vibration source).

As many, i.e. four, microphones $61_1$–$61_4$ are provided for receiving cancelling sounds.

Four loud speakers $62_1$–$62_4$, $63_1$–$63_4$ are provided for a low frequency range and a high frequency range, respectively.

An adaptive control circuit 64 is comprised of a low frequency-band processor 65, a high frequency-band processor 66, and a control 67 for controlling the processors 65, 67. The processors 65, 66 are formed of digital signal processors (DSP) capable of effecting high speed calculations.

In the road noise control system constructed as above, noise signals from the noise sensors $60_1$–$60_4$ are delivered via respective amplifiers $68_1$–$68_4$ and respective anti-aliasing filters $69_1$–$69_4$ to a divided processing circuit (first and second divided processing circuits) 70.

In the divided processing circuit 70, the low frequency noise signals are oversampled by an A/D converter $71_1$, and the high frequency noise signals by an A/D converter $71_2$, respectively, and the oversampled noise signals are input as reference signals X to the adaptive control circuit 64. Cancelling signals formed by the low frequency-band processor 65 are converted to analog signals by D/A converters $72_1$, $71_2$. The analog signals are fed through low pass filters $73_1$–$73_4$ and amplifiers $74_1$–$74_4$ to the loud speakers $62_1$–$62_4$ to be output therefrom. On the other hand, cancelling signals from the high frequency-band processor 66 are converted to analog signals by D/A converters $75_1$, $75_2$, and the analog signals are fed through low pass filters $76_1$–$76_4$ and amplifiers $77_1$–$77_4$ to the loud speakers $63_1$–$63_4$ to be output therefrom. Cancelling sounds from the loud speakers $62_1$–$62_4$, $63_1$–$63_4$ are received by the microphones $61_1$–$61_4$ together with noise (primary noise) directly transmitted from the noise sources, and error signals indicative of the error between the two inputs (cancelling error) are fed through amplifiers $78_1$–$78_4$ and anti-aliasing filters $79_1$–$79_4$ and oversampled by A/D converters $80_1$, $80_2$ into digital data. The digitalized error signals $\epsilon$ are fed back to the adaptive control circuit 64 for formation of cancelling signals having inverse transfer characteristics.

As described in detail above, the active vibration control system according to the invention is provided with divided processing means which divides vibration sensed by vibration sensing means into vibration components falling respectively within a plurality of frequency ranges and separately processing the divided components. The divided processing means has sampling means which samples the vibration components within the frequency ranges at different sampling periods between the frequency ranges. Therefore, the divided components can be processed in different manners suitable to the respective different frequency ranges to thereby enable achieving improved noise suppression over a wide frequency range.

More specifically, vibration components within a high frequency range may be oversampled so that even short waveform information contained in the noise can be accurately retained to enable accurate signal processing and hence effective suppression of noise. On the other hand, vibration components within a low frequency range may be downsampled to enable simplification of the control system as well as formation of a cancelling signal having high identification accuracy.

Further, the divided processing means may effect signal processing in different algorithmic manners appropriate to respective frequency ranges within which the noise components fall, to thereby further effectively suppress noise.

Moreover, the active vibration control system according to the invention may have single cancelling vibration-generating means, and synthetic inputting means for synthesizing cancelling signals formed for respective different frequency ranges, to thereby simplify the construction of the system and reduce the manufacturing cost.

Alternatively, the active vibration control system according to the invention may have a plurality of cancelling vibration-generating means corresponding, respectively, to as many different frequency ranges, and separate inputting means for separately inputting cancelling signals formed for the respective different frequency ranges to the respective cancelling vibration-generating means, to improve the responsiveness of the cancelling vibration-generating means and hence obtain more accurate cancelling effects over a wide frequency range for further effective suppression of vibration or noise.

What is claimed is:

1. An active vibration control system comprising:

at least one vibration source;

at least one first sensor means for sensing vibration from said vibration source;

control means disposed to receive an output from said first sensor means as a reference signal, said control means being responsive to said reference signal for generating a cancelling signal having a transfer characteristic inverse to a transfer characteristic of vibration from said vibration source to a human body;

cancelling vibration-generating means responsive to an output from said control means for generating cancelling vibration; and second sensor means for sensing an error between said vibration from said vibration source and said cancelling vibration from said cancelling vibration-generating means and for generating an error signal indicative of the sensed error, wherein said control means varies said inverse transfer characteristic of said cancelling signal by an amount corresponding to a value of said error signal so as to minimize said error;

said control means comprising divided processing means including oversampling means for oversampling outputs from said first and second sensor means, filter means for dividing the oversampled outputs from said first and second sensor means into vibration components falling respectively within a plurality of frequency ranges including at least a high frequency range and a low frequency range, downsampling means for downsampling said vibration components falling within said low frequency range, and processing means for separately processing said vibration components falling within said high frequency range from said filter means and the downsampled vibration components falling within said low frequency range by FIR type adaptive digital filters.

2. An active vibration control system as claimed in claim 1, wherein said divided processing means processes said vibration components by the use of different algorithmic methods for said plurality of frequency ranges respectively.

3. An active vibration control system as claimed in claim 1, including single cancelling vibration-generating means forming said cancelling vibration-generating means, and synthetic inputting means for synthesizing a plurality of cancelling signals formed by processing said vibration components within said plurality of frequency ranges by said divided processing means and inputting the synthesized cancelling signal to said single cancelling vibration-generating means.

4. An active vibration control system as claimed in claim 1, including a plurality of said cancelling vibration-generating means and corresponding, respectively, to said plurality of frequency ranges, and separate inputting means for separately inputting a plurality of cancelling signals formed by processing said vibration components within said plurality of frequency ranges by said divided processing means, respectively, to said plurality of cancelling vibration-generating means.

5. An active vibration control system as claimed in claim 1, wherein including a plurality of said cancelling vibration-generating means and corresponding, respectively, to said plurality of frequency ranges, and separate inputting means for separately inputting a plurality of cancelling signals formed by processing said vibration components within said plurality of frequency ranges by said divided processing means, respectively, to said plurality of said cancelling vibration-generating means, wherein, a plurality of said second sensor means corresponding, respectively, to said plurality of frequency ranges.

* * * * *